(12) United States Patent
Haisma et al.

(10) Patent No.: US 8,562,511 B2
(45) Date of Patent: Oct. 22, 2013

(54) SYSTEM FOR INDUCING A SUBJECT TO FALL TO SLEEP

(75) Inventors: Nicoline Haisma, Eindhoven (NL); Gerrit-Jan Bloem, Eindhoven (NL); Gerard David La Hei, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 971 days.

(21) Appl. No.: 12/282,186

(22) PCT Filed: Feb. 28, 2007

(86) PCT No.: PCT/IB2007/050645
§ 371 (c)(1),
(2), (4) Date: Sep. 9, 2008

(87) PCT Pub. No.: WO2007/105127
PCT Pub. Date: Sep. 20, 2007

(65) Prior Publication Data
US 2009/0062598 A1 Mar. 5, 2009

(30) Foreign Application Priority Data
Mar. 14, 2006 (EP) .................................. 06111097

(51) Int. Cl.
*A61M 21/00* (2006.01)
(52) U.S. Cl.
USPC ............................................................ 600/27

(58) Field of Classification Search
USPC ................................ 600/26–28; 128/897, 898
See application file for complete search history.

(56) References Cited

U.S. PATENT DOCUMENTS

| | | | |
|---|---|---|---|
| 5,167,610 A * | 12/1992 | Kitado et al. | 600/26 |
| 6,212,135 B1 * | 4/2001 | Schreiber | 368/107 |
| 6,720,743 B2 | 4/2004 | Yano et al. | |
| 2005/0143617 A1 | 6/2005 | Auphan | |
| 2005/0209504 A1 * | 9/2005 | Elliott | 600/26 |
| 2006/0205994 A1 * | 9/2006 | Sunnen | 600/27 |

FOREIGN PATENT DOCUMENTS

| | | |
|---|---|---|
| GB | 670789 A | 4/1952 |
| GB | 2035088 A | 6/1980 |
| WO | 9306575 A1 | 4/1993 |
| WO | 2004014226 A1 | 2/2004 |
| WO | 2005055802 A2 | 6/2005 |

* cited by examiner

*Primary Examiner* — Samuel Gilbert

(57) ABSTRACT

A system for inducing a subject to fall to sleep includes a light pattern generator for generating a time varying light pattern in view of the subject. Further, the system includes a breathing rate measuring unit for measuring a breathing frequency of the subject. In addition, the system includes a control unit connected to the breathing rate measuring unit and the light pattern generator, for controlling the light pattern generator such that the generated light pattern has a pattern frequency substantially between the measured breathing frequency and a pre-selected desired frequency.

19 Claims, 4 Drawing Sheets

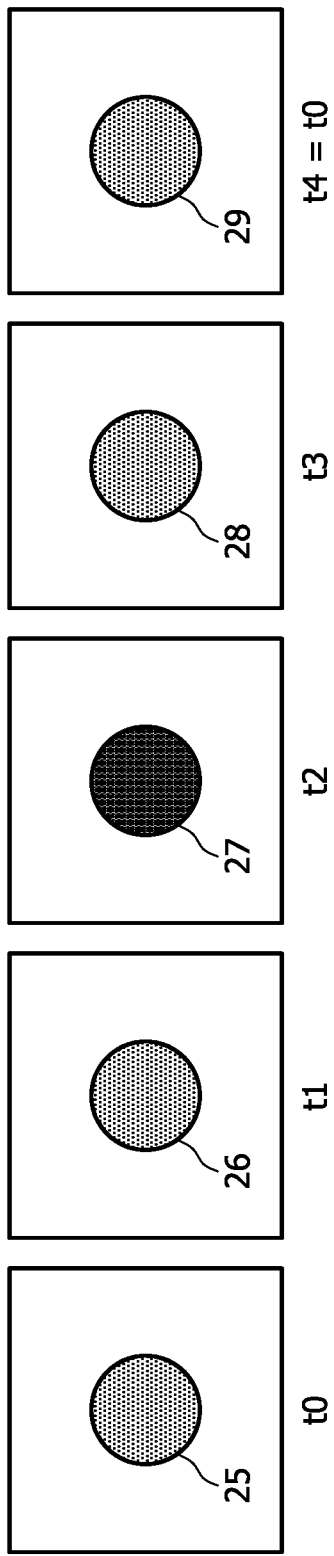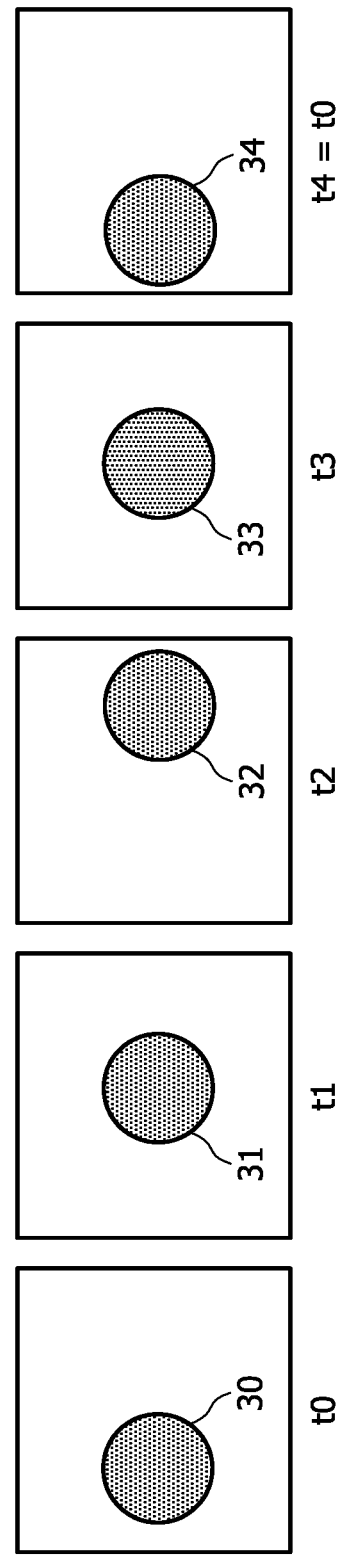
FIG. 4
FIG. 5

SYSTEM FOR INDUCING A SUBJECT TO FALL TO SLEEP

TECHNICAL FIELD

The invention relates to a system for inducing a subject to fall to sleep.

BACKGROUND TO THE INVENTION AND PRIOR ART

Getting to sleep may not always be as self-evident as one would wish. Among causes of not falling to sleep are being overtired, pain and/or stress. It is known to arrange bedrooms to provide optimal conditions for inducing a subject suffering a pathologic insomnia to fall to sleep, such as a comfortable bed, minimum light and reduced sound parameters. In addition, medications are known which render patients sleepy. However, it is also known that taking repeatedly such medication is not necessarily beneficial to one's health.

Further, from U.S. Pat. No. 5,167,610 a sleep inducing system is known based on a respiration cycle detected as a biological signal.

From the prior art also sleep and environment control systems are known to guide control processes, e.g. US 2005/0143617. The system disclosed in US '617 includes a respiration sensor capable of gathering sleep data from a person and environment data during sleep using light as an environment control interface.

However, it has been found that conventional systems may not satisfactory induce sleep in the subject.

It is therefore an object of the present invention to provide an improved system for inducing a subject to fall to sleep.

SUMMARY OF THE INVENTION

According to a first aspect of the invention, there is provided a system for inducing a subject to fall to sleep, comprising a light pattern generator for generating a time varying light pattern in view of the subject; a breathing rate measuring unit for measuring a breathing frequency of the subject; and a control unit connected to the breathing rate measuring unit and the light pattern generator, for controlling the light pattern generator, such that the generated light pattern has a pattern frequency substantially between the measured breathing frequency and a pre-selected desired frequency.

The invention is partly based on the observation that persons normally have a relatively low breathing frequency during a first stage of their sleep.

The invention is further also based on the insight that persons tend to synchronize their breathing rhythm to a cycle of light patterns, which they observe.

By providing a light pattern generator a time varying light pattern can be generated in view of the subject, so that the subjects attention is directly or indirectly drawn to the time varying light pattern. The breathing rate measuring unit is arranged to measure the actual breathing frequency of the subject. Further, by controlling the light pattern generator, such that the generated light pattern has a pattern frequency substantially between the measured breathing frequency and the pre-selected desired frequency, a light pattern is obtained that has a lower frequency than the actual breathing frequency, thereby leading the subject to the pre-selected desired frequency. By choosing the pre-selected desired frequency to a value that corresponds to a breathing frequency of the subject wherein he/she falls to sleep, the subject is thus deduced to reduce the breathing frequency to a breathing frequency approaching the frequency that is natural when he/she falls to sleep. In doing so, the breathing frequency is a parameter, which is controlled in a control loop. Thereby, the breathing frequency is brought in a more optimal status for falling to sleep in a relatively natural manner, hence inducing the subject to actually falling to sleep.

In a preferred embodiment, the system comprises elements for forming a control loop of the breathing frequency of the subject.

It is noted that the pre-selected desired frequency might be chosen to be an optimal breathing frequency averaged over a multiple set of persons. The pre-selected desired frequency might also correspond to the breathing frequency of persons falling to sleep having person characteristics in common with the subject which is induced to fall to sleep, e.g. persons of a similar age, sex, etc. Moreover, the pre-selected desired frequency might correspond to the breathing frequency of the subject himself or herself when falling to sleep, thus personalizing the system to the subject in question. Thereto, in a preferred embodiment according to the invention the pre-selected desired frequency is one, which has been found to bring on a sleeping state in the subject. In general, the pre-selected desired frequency is lower than an actual breathing frequency of a subject that is not sleeping.

After repeated application of the abovementioned steps of measuring the actual breathing frequency and controlling the light pattern generator, such that the generated light pattern has a pattern frequency substantially between the measured breathing frequency and the pre-selected desired frequency, the subject is deduced to reduce the breathing frequency further, thereby approaching the pre-selected desired frequency further, and hence further improving falling to sleep conditions. Then, the measured breathing frequency, the pre-selected desired frequency and the pattern frequency substantially coincide. Optionally, the system for inducing a subject to fall to sleep, or at least the light pattern generator is switched off.

In a preferred embodiment according to the invention, the system further comprises a differentiator for determining a difference frequency between the breathing frequency and the pre-selected desired frequency, wherein the system is further arranged to determine the pattern frequency using the difference frequency and the breathing frequency. By using a differentiator the difference frequency to be eliminated can easily be determined. Further, by using the difference frequency and the measured breathing frequency, a new pattern frequency can be determined that might be selected between the actual breathing frequency and the pre-selected frequency.

In a further preferred embodiment the system comprises a limiter to which a signal representing the difference frequency is input to determine the pattern frequency, so that the pattern frequency can simply be obtained by adding the limited difference frequency and the actual measured breathing frequency, the sum being between the actual breathing frequency and the pre-selected frequency by definition.

In a preferred embodiment according to the invention, the limiter is arranged to limit the difference frequency between a pre-selected minimum limit value and a pre-selected maximum limit value. In this way a simple, robust algorithm is obtained for leading the breathing frequency to the pre-selected frequency.

In an alternative embodiment according to the invention, the limiter is arranged to limit the difference frequency between an adaptable minimum limit value and an adaptable maximum limit value, thereby offering possibilities to adapt the minimum and maximum limit values of the limiter during the process of reducing the breathing frequency of the subject. As an example, the minimum and maximum limit values could be adapted in response to the response of the subject to the proposed breathing frequency. It is noted that it is not necessary to provide a limiter with adaptable limit values. Due to the limiting processing step of the limiter, the breathing frequency of the subject is smoothly adjusted to the pre-selected desired frequency. However, by increasing the limit values, the light pattern frequency will deviate more from the breathing frequency of the subject, so that it is harder for the subject to synchronize with the pattern frequency. By decreasing the limit values, the light pattern frequency will deviate less from the breathing frequency of the subject, thereby making it easier for the subject to synchronize. On the other hand, it will take longer before the subject will reach the desired breathing frequency.

In a preferred embodiment according to the invention, the control unit is also connected to a sound generating system for generating a time varying sound, such that a cycle of the time varying sound substantially equals the pattern frequency. In doing so, the subject might be further tend to synchronize his/her breathing frequency with the pattern frequency, so that an optimal condition for falling to sleep is faster reached and/or chances that the subject will tend to adapt his/her breathing frequency to the desired frequency, improve.

In a preferred embodiment according to the invention, the time varying light pattern comprises a sequence with objects having different optical properties, such as different shapes, different colors, different positions, and/or different light intensities, so that light patterns having different optical images can be observed by the subject in order to close the above-mentioned control loop.

In a further preferred embodiment according to the invention, the system is arranged such that the light pattern objects become brighter, larger, have a larger wavelength and/or move from left to right during an exhale stage of the subject and that the light pattern objects become dimmer, smaller, have a smaller wavelength and/or move from right to left during an inhale stage of the subject. It has been observed that subjects tend to synchronize their breathing frequency with the pattern frequency easier when the light intensity, the size, the wavelength and/or the position of an object in the light pattern is synchronized with the actual breathing cycle as indicated above.

According to a second aspect of the present invention, there is provided a method for inducing a subject to fall to sleep, comprising the steps of measuring a breathing frequency of the subject; selecting a pattern frequency between the breathing frequency and a pre-selected desired frequency; generating in view of the subject a time varying light pattern having the pattern frequency; and repeating the above-mentioned steps at a plurality of time intervals.

According to a third aspect of the present invention, there is provided a computer program product for processing data to induce a subject to fall to sleep, which computer program product comprises instructions for causing a processor to perform the steps of selecting a pattern frequency between a measured breathing frequency of a subject and a pre-selected desired frequency, for generating in view of the subject a time varying light pattern having the pattern frequency; and repeating the above-mentioned steps at a plurality of time intervals.

According to a fourth aspect of the present invention, there is provided a computer system, comprising a computer station being arranged to induce a subject to fall to sleep by performing the steps of selecting a pattern frequency between a measured breathing frequency of a subject and a pre-selected desired frequency, for generating in view of the subject a time varying light pattern having the pattern frequency; and repeating the above-mentioned steps at a plurality of time intervals.

BRIEF DESCRIPTION OF THE DRAWINGS

In order that the invention may be more fully understood, embodiments thereof will now be described by way of example only, with reference to the figures in which:

FIG. 4 shows a third light pattern sequence;

FIG. 5 shows a fourth light pattern sequence, and

DESCRIPTION OF THE PREFERRED EMBODIMENTS

The figures are merely schematic views of preferred embodiments according to an embodiment of the invention. In the figures, the same reference numbers refer to equal or corresponding parts.

Figure 1:
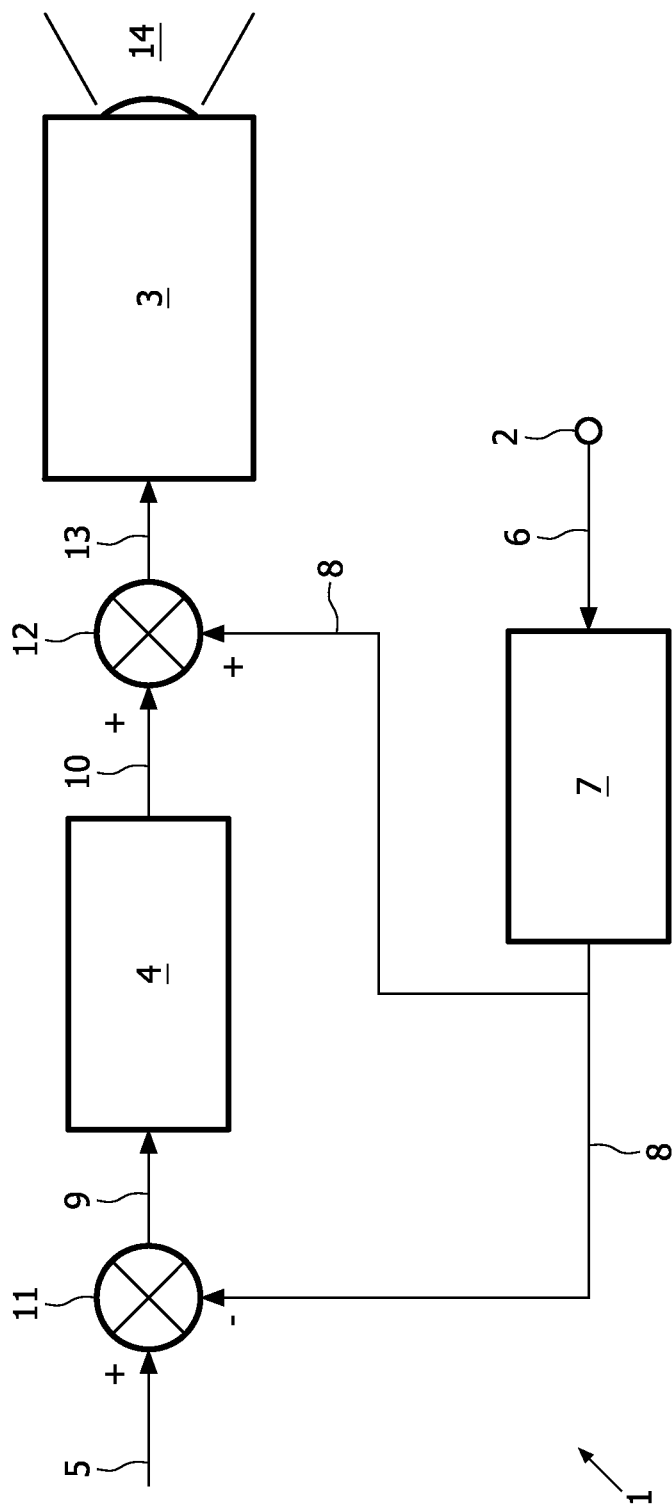
FIG. 1 shows a sleep inducing system according to an embodiment of the present invention.

FIG. 1 shows a system 1 for inducing a subject to fall to sleep according to the invention. The system 1 comprises a breathing rate measuring unit 2 for measuring a breathing frequency 6 of the subject. The unit 2 might e.g. comprise one or more acoustic, flow and/or optical sensors and is preferably attached to the subject or installed in the bed or other suitable location, such as a chair etc. of the subject.

Further, the system comprises a light pattern generator 3 for generating a time varying light pattern in view of the subject. The generator comprises means for projecting an image 14 on a surface, such as a screen, wall and/or a ceiling near the subject, so that the subject can observe the light pattern that is generated.

The system is also provided with a control unit connected to both the breathing rate measuring unit 2 and to the light pattern generator 3. The control unit comprises an adder 12 and is arranged to control the light pattern generator 3, such that the generated light pattern has a pattern frequency 13 between the measured breathing frequency 8 and a pre-selected desired frequency 5.

Further, the system comprises a differentiator 11 for determining a signal representing a difference frequency 9 between the breathing frequency 8 and the pre-selected desired frequency 5, wherein the system is further arranged to determine the pattern frequency 13 using the difference frequency and the breathing frequency. In this process, the pattern frequency is selected between the breathing frequency and the pre-selected desired frequency. To that end, the system further comprises elements, among others the breathing rate measuring unit 2, the differentiator 11 and the control unit, for forming a control loop of the breathing frequency of the subject.

The system further comprises a limiter 4 to which a signal 9 representing the difference frequency is input to determine the above-mentioned pattern frequency 13. The output signal of the limiter 4 is input to a first input port of an adder 12. The breathing frequency 8 is input to a second input port of the adder 12, so that the adder 12 computes the sum of the limited difference signal 9 and the breathing frequency to obtain the pattern frequency 13.

It is noted in this context that information carried on a signal is presented as such or as the information itself. As an example, in this context a pattern frequency is similar to a pattern frequency signal.

In the embodiment shown in FIG. 1, the measured breathing frequency is fed to a frequency analyzer 7, e.g. for applying a band-pass filter to the measured data. The frequency analyzer is further arranged to output a signal that is a measure for the measured breathing frequency.

In one embodiment the limiter 4 is arranged to limit the difference frequency between a pre-selected minimum limit value and a pre-selected maximum limit value. In a further embodiment the limiter 4 is arranged to limit the difference frequency between an adaptable minimum limit value and an adaptable maximum limit value. By adapting the limit values one can synchronize the actual breathing frequency smoothly to the pre-selected desired frequency.

The pre-selected desired frequency is one, which has been found to bring on a sleeping state in the subject.

In addition, the control unit is further connected to a sound generating system for generating a time varying sound, such that a cycle of the time varying sound substantially equals the pattern frequency.

The time varying light pattern comprises a sequence with objects having different shapes, colors, positions and/or light intensities. Examples of such object sequences are shown in FIGS. 2-5.

Figure 2:
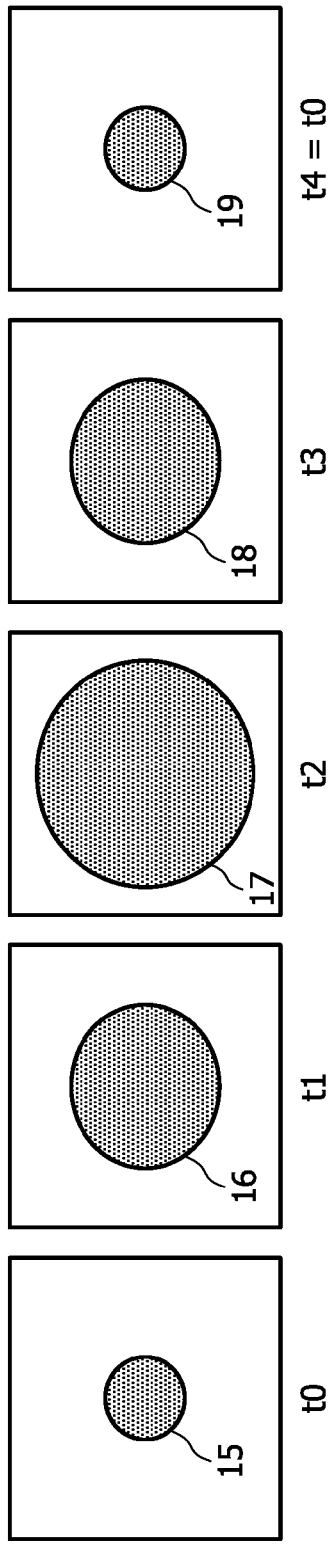
FIG. 2 shows a first light pattern sequence.

FIG. 2 shows a first light pattern sequence wherein an object sequence 15-19 comprises objects having different shapes, in particular a disc 15-19 having different diameters. The left window shows the pattern at a start instant t0, the window adjacent the left window shows the pattern at a first instant t1, and so on until a fourth instant t4 is reached wherein the cycle of the varying light pattern closes. The pattern at the fourth instant t4 therefore equals the start instant t0. The shape of the objects 15-19 may also vary by changing the outer perimeter of the object, e.g. by changing a disc to a triangular, etc. In this way, a variety of different shaped objects can be projected.

Figure 3:
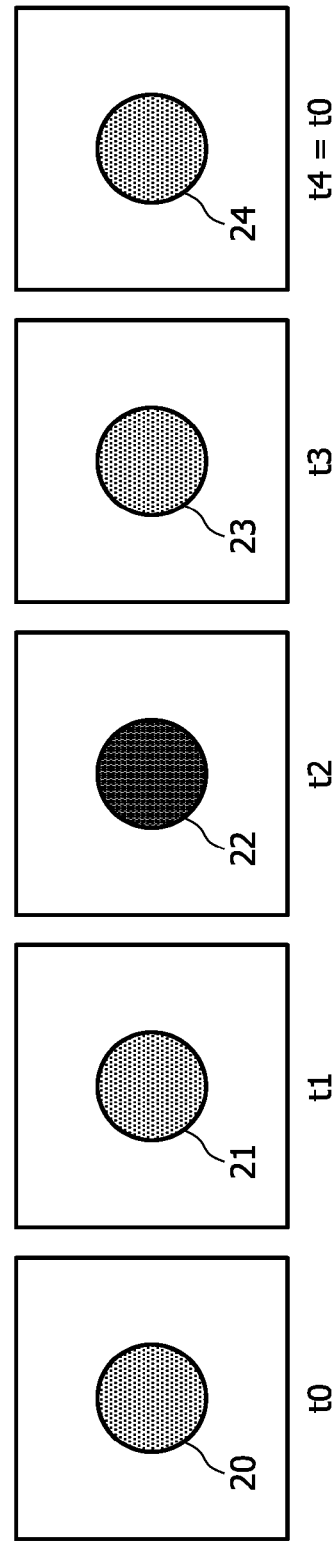
FIG. 3 shows a second light pattern sequence.

Similarly, FIGS. 3-5 show a second, third and fourth light pattern sequence respectively, wherein object sequences 20-24, 25-29 and 30-34 comprise objects having different colors, positions and light intensities, respectively.

Figure 6:
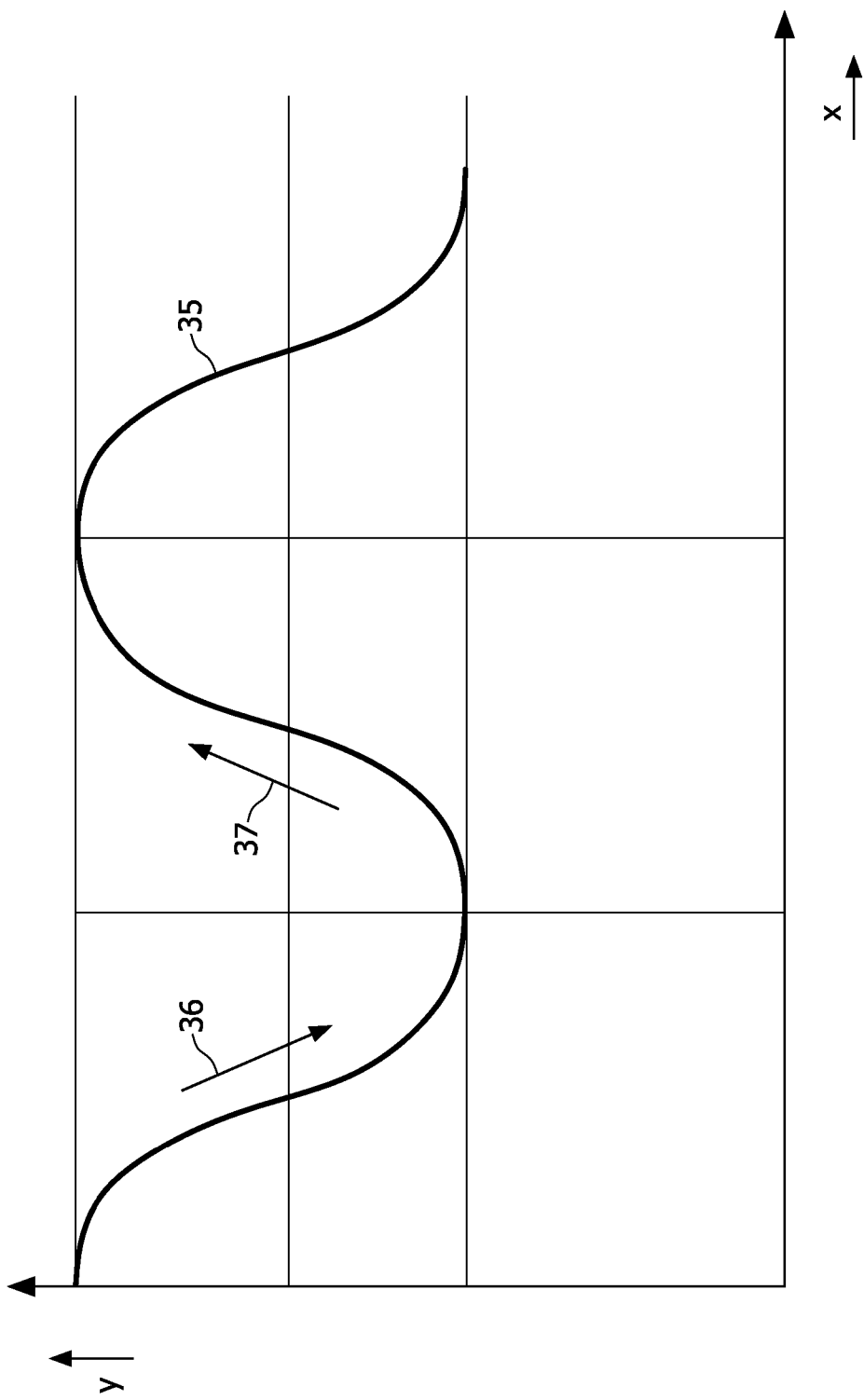
FIG. 6 shows a breathing cycle of a subject.

FIG. 6 shows a breathing cycle 35 of a breathing parameter Y of a subject as a function of time X. A first arrow 36 indicates an exhale phase and a second arrow 37 indicates an inhale phase, respectively of the breathing cycle 35. According to an embodiment of the invention, the system 1 may be arranged such that the light pattern objects 30-34 in FIG. 5 become brighter during an exhale stage of the subject and the light pattern objects 30-34 may become dimmer during an inhale stage of the object.

It is noted that the system could also be arranged such that the light pattern objects become larger, have a larger wavelength and/or move from left to right during an exhale stage of the subject and that the light pattern objects become smaller, have a smaller wavelength and/or move from right to left during an inhale stage of the subject. As an example, the wavelength of such an object might change from blue to red during an exhale stage and change from red to blue again during an inhale stage of the subject.

Further, as the person skilled in the art will understand, combinations of object variations could be made, e.g. an object that both changes position and light intensity. Also multiple objects could be projected in the light pattern.

The invention is not restricted to the embodiments described herein. It will be understood that many variants are possible.

Instead of using a limiter also other elements could be used to process the difference signal, e.g. a processing filter.

Further, as the person skilled in the art will understand, the frequency analyzer can also be used for performing further processing steps on the measured breathing data, such as a time to frequency transformation, frequency measuring, and/or other filter techniques in order to extract a base frequency of the subject's breathing.

In addition, it is noted that signals in the system shown in FIG. 1 can be analogous or can be converted to digital signals, especially if a computer system is applied to process data. The computer system thereto comprises a computer station.

Whilst specific embodiments of the invention have been described above, it will be appreciated that the invention may be practiced otherwise than as described. The description is not intended to limit the invention. Any reference signs in the claims shall not be construed as limiting the scope.

The invention claimed is:

1. A system for inducing a subject to fall to sleep comprising:
    a light pattern generator for generating a time varying light pattern in view of the subject;
    a breathing rate measuring unit for measuring a breathing frequency of the subject;
    a control unit connected to the breathing rate measuring unit and the light pattern generator, for controlling the light pattern generator such that the generated light pattern has a pattern frequency substantially between the measured breathing frequency and a pre-selected desired frequency; and
    a differentiator for determining a difference frequency between the breathing frequency and the pre-selected desired frequency, wherein the system is further configured to determine the pattern frequency using the difference frequency and the breathing frequency.

2. The system according to claim 1, further comprising elements for forming a control loop of the breathing frequency of the subject.

3. The system according to claim 1, further comprising a limiter to which a signal representing the difference frequency is input to determine the pattern frequency.

4. The system according to claim 3, wherein the limiter is arranged to limit the difference frequency between a pre-selected minimum limit value and a pre-selected maximum limit value.

5. The system according to claim 3, wherein the limiter is arranged to limit the difference frequency between an adaptable minimum limit value and an adaptable maximum limit value.

6. The system according to claim 1, wherein the pre-selected desired frequency is one, which has been found to bring on a sleeping state in the subject.

7. The system according to claim 1, wherein the control unit further is connected to a sound generating system for generating a time varying sound, such that a cycle of the time varying sound substantially equals the pattern frequency.

8. The system according to claim 1, wherein the time varying light pattern comprises a sequence of the objects having different shapes.

9. The system of claim 1, wherein the control unit comprises an adder for adding the difference frequency with the breathing frequency for generating the light pattern.

10. The system of claim 1, wherein the control unit is configured to control the light pattern generator such that a color of light pattern objects of the generated light pattern increases in wavelength and the light pattern objects move in a first direction during an exhale stage of the subject, and the color of the light pattern objects decreases in wavelength and the light pattern objects move in a second direction during an inhale stage of the subject, and wherein the first direction is different from the second direction.

11. A method for inducing a subject to fall to sleep, comprising the acts of:
measuring a breathing frequency of the subject;
selecting a pattern frequency substantially between the breathing frequency and a pre-selected desired frequency;
determining by a differentiator a difference frequency between the breathing frequency and the pre-selected desired frequency;
determining the pattern frequency using the difference frequency and the breathing frequency;
generating by a light pattern generator in view of the subject a time varying light pattern having the pattern frequency; and
repeating the measuring, selecting and generating acts at a plurality of time intervals until the breathing frequency reaches the pre-selected desired frequency indicating that the subject falls asleep.

12. The method of claim 11, further comprising the act of controlling by control unit the light pattern generator such that the generated time varying light pattern has a pattern frequency substantially between the measured breathing frequency and the pre-selected desired frequency, wherein the control unit comprises an adder for adding the difference frequency with the measured breathing frequency for generating the time varying light pattern.

13. The method of claim 11, wherein the generating act generates the light pattern such that a color of light pattern objects of the generated light pattern increases in wavelength and the light pattern objects move in a first direction during an exhale stage of the subject, and the color of the light pattern objects decreases in wavelength and the light pattern objects move in a second direction during an inhale stage of the subject, and wherein the first direction is different from the second direction.

14. A computer system, comprising a computer station being arranged to induce a subject to fall to sleep by performing the acts of:
selecting a pattern frequency substantially between a measured breathing frequency of a subject and a pre-selected desired frequency;
determining by a differentiator a difference frequency between the measured breathing frequency and the pre-selected desired frequency;
determining the pattern frequency using the difference frequency and the breathing frequency;
generating by a light pattern generator in view of the subject a time varying light pattern having the pattern frequency; and
repeating the selecting act at a plurality of time intervals.

15. The computer system of claim 14, wherein the computer system is further arranged to control the light pattern generator such that the generated time varying light pattern has a pattern frequency substantially between the measured breathing frequency and the pre-selected desired frequency, and wherein the computer system further comprises an adder for adding the difference frequency with the measured breathing frequency for generating the time varying light pattern.

16. The computer system of claim 14, wherein the selecting act includes generating the light pattern such that a color of light pattern objects of the generated light pattern increases in wavelength and the light pattern objects move in a first direction during an exhale stage of the subject, and the color of the light pattern objects decreases in wavelength and the light pattern objects move in a second direction during an inhale stage of the subject, and wherein the first direction is different from the second direction.

17. A non-transitory computer readable medium embodying computer instructions for inducing a subject to fall to asleep, wherein the computer instructions, when executed by a processor, configure the processor to perform the acts of:
selecting a pattern frequency substantially between a measured breathing frequency of a subject and a pre-selected desired frequency;
determining by a differentiator a difference frequency between the measured breathing frequency and the pre-selected desired frequency;
determining the pattern frequency using the difference frequency and the breathing frequency;
generating by a light pattern generator in view of the subject a time varying light pattern having the pattern frequency; and
repeating the selecting act at a plurality of time intervals.

18. The non-transitory computer readable medium of claim 17, wherein the computer instructions further configure the processor to control a light pattern generator such that the generated time varying light pattern has a pattern frequency substantially between the measured breathing frequency and the pre-selected desired frequency, and to add the difference frequency with the measured breathing frequency for generating the time varying light pattern.

19. The non-transitory computer readable medium of claim 17, wherein the selecting act includes generating the light pattern such that a color of light pattern objects of the generated light pattern increases in wavelength and the light pattern objects move in a first direction during an exhale stage of the subject, and the color of the light pattern objects decreases in wavelength and the light pattern objects move in a second direction during an inhale stage of the subject, and wherein the first direction is different from the second direction.

* * * * *